United States Patent [19]

Fung et al.

[11] Patent Number: 5,405,773
[45] Date of Patent: * Apr. 11, 1995

[54] ASSAY FOR MOTILE FACULTATIVE ANAEROBIC PATHOGENS

[75] Inventors: Daniel Y. C. Fung; Linda Yu, both of Manhattan, Kans.

[73] Assignee: Kansas State University Research Foundation, Manhattan, Kans.

[*] Notice: The portion of the term of this patent subsequent to Feb. 16, 2010 has been disclaimed.

[21] Appl. No.: 119,457

[22] Filed: Sep. 10, 1993

Related U.S. Application Data

[63] Continuation of Ser. No. 936,529, Aug. 28, 1992, abandoned, which is a continuation of Ser. No. 594,647, Oct. 9, 1990, Pat. No. 5,187,070.

[51] Int. Cl.$^6$ .......................... C12N 1/00; C12Q 1/26
[52] U.S. Cl. ...................... 435/243; 435/25; 435/244; 435/252.1; 435/253.6; 435/801
[58] Field of Search ................ 435/243, 25, 29, 34, 435/240.2, 240.3, 244, 252.1, 253.6, 801

[56] References Cited

U.S. PATENT DOCUMENTS 4,996,073  2/1991  Copeland et al. .................. 435/801
5,187,070  2/1993  Fung et al. ............................ 435/25

OTHER PUBLICATIONS

Compiled by Jesse Ostnoff "FSIS Method for Isolation and Identification of Salmonella, *Listeria Monocytogenes*, and *Campylobacter Jejuni* in Meat and Poultry Carcasses" *National Agricultural Library*, Sep. 1989.

Cassiday et al., *Applied and Environmental Microbiology*, vol. 56, No. 7, pp. 2274–2275, Jul. 1990.

Oxyrase Inc., *Technical bulletin*, "Properties of the Oxyrase Enzyme System Used to Isolate and Cultivate Anaerobic Microorganisms" Ashland, Ohio 44805.

Adler, *Critical Reviews in Biotechnology*, vol. 10, No. 2, pp. 119–127, 1990.

Adler et al, *J. Bacteriology*, vol. 147, No. 2, pp. 326–332, Aug. 1981.

*Primary Examiner*—Michael G. Wityshyn
*Assistant Examiner*—Abdel A. Mohamed
*Attorney, Agent, or Firm*—Hovey, Williams, Timmons & Collins

[57] ABSTRACT

An approved assay for the determination for motile facultative anaerobic pathogens is described which involves the use of a growth-enhancing substance such as oxyrase enzyme in order to increase the growth rate of a target pathogen in a growth medium, to thereby shorten the time required to complete the assay. The assay of the invention is particularly suited for the determination of *L. monocytogenes* in food products such as meat and dairy goods, and provides an effective screening assay which can be completed in about 24–36 hours. Preferably, a product sample is first incubated in Fraser Broth containing oxyrase enzyme; if a darkened color results, a small portion of the liquid is then placed within a U-shaped culture tube provided with modified Oxford agar; the motility characteristics of the target pathogen are observed in the U-tube, which is indicative of the presence of *L. monocytogenes*.

3 Claims, 5 Drawing Sheets

ASSAY FOR MOTILE FACULTATIVE ANAEROBIC PATHOGENS

This application is a continuation of application Ser. No. 07/936,529, filed Aug. 28, 1992, now abandoned which is a continuation of Ser. No. 07/594,647, filed Oct. 9, 1990, now U.S. Pat. No. 5, 187,070.

BACKGROUND OF THE INVENTION

1. Field of the Invention

The present invention is broadly concerned with an improved assay for the determination of motile facultative anaerobic pathogens, and especially *L. monocytogenes*, in samples such as meat. More particularly, it is concerned with such an assay which makes use of a substance such as an oxygen-reactive enzyme (e.g., oxyrase enzyme) for enhancing the growth rate of a target pathogen in a selected growth medium, in order to materially lessen the amount of time required for completing the assay. Assays for determining the presence of *L. monocytogenes* in meat samples can be completed in times many hours shorter than previous standard assays.

2. Description of the Prior Art

*Listeria monocytogenes* is a motile facultative anaerobic pathogen which can cause various diseases in man, including meningoencephalitis, low-grade septicemia, infectious mononucleosis-like syndrome, pneumonia, endocarditis, bacterial aortic aneurysm, localized abscesses, papular or pustular cutaneous lesions, conjunctivitis and urethritis. It is known that the pathogen can be transmitted from the eating of infected meat or milk. Accordingly, because of the pernicious effects of this pathogen, and its increasing incidence in human foods, there has been a significant increase in the concern expressed about *L. monocytogenes* and its effects on human health.

The accepted present-day assay for *L. monocytogenes* is described in "FSIS Method for the Isolation and Identification of *Listeria monocytogenes* From Processed Meat and Poultry Products", Laboratory Communication No. 57, May 24, 1989, distributed by the USDA and others; this publication is incorporated by reference herein. Broadly speaking, the FSIS assay involves placing a sample of meat in UVM Broth followed by incubation at 30° C. for 24 hours. A 0.1 ml. aliquot of the incubated mixture is then placed in 10 ml. of Fraser Broth and incubated at 30° C. or 24–48 hours. If the Fraser Broth darkens, the liquid is swabbed onto a modified Oxford agar plate, which is then incubated at 35° C. for 24–48 hours. The incubated plates are then examined for *L. monocytogenes* colonies exhibiting characteristic surrounding black zones resulting from hydrolyzed esculin. Suspected colonies of *L. monocytogenes* are then gently touched with an inoculation needle and are streaked for isolation onto a Horse Blood Overlay Agar plate. These plates are incubated overnight at 35° C. Thereafter, the plates are examined under a fluorescent lamp and translucent colonies are then further screened and subjected to conventional confirming tests.

Generally speaking, the prior *L. monocytogenes* assay involves a total time of from 56–72 hours. This represents a real difficulty for the food processor, in that food otherwise ready for shipment must be held pending the completion of assay screening. Accordingly, there is a real need in the art for an effective assay for *L. monocytogenes* (or other motile facultative anaerobic pathogens) which can be successfully performed in a significantly shorter period of time.

SUMMARY OF THE INVENTION

The present invention overcomes the problems outlined above and provides an improved assay for motile facultative anaerobic pathogens which in the case of *L. monocytogenes* can be completed in a total time of from about 24–36 hours. Broadly, the assay of the invention is designed to determine the presence of target pathogens in a product sample (e.g. beef or other meats) capable of supporting the growth of such pathogens. The assay includes the steps of first incubating the sample in a growth medium containing an agent such as esculin which will change the color of the medium in the presence of the target pathogen. If such a characteristic color change is observed, the motility characteristics of the pathogen for the color change is determined. The specific improvement of the invention involves contacting the product sample during the incubation step with an effective amount of a substance which enhances the growth rate of the target pathogen, this substance being selected from the group consisting of growth-stimulating effective reducing agents and oxygen-reactive enzymes. In particularly preferred forms, the growth medium is Fraser Broth, a known medium commercialized by, inter alia, Beeton Dickinson Microbiology Systems of Cockeysville, Md. A copy of a Becton Dickinson "Product Information Sheet" relative to the Fraser Broth is incorporated by reference herein. While Fraser Broth is the preferred medium, those skilled in the art will appreciate that other media can also be employed, so long as the media contains the described color-change agent.

The most preferred growth-enhancing substance is oxyrase enzyme, known to be an effective oxygen-reducing enzyme used to produce anaerobic conditions. The oxyrase enzyme is described in a technical bulletin "Properties of the Oxyrase Enzyme System Used to Isolate and Cultivate Anaerobic Microorganisms", distributed by Oxyrase, Inc. of Ashland, Ohio. Moreover, the enzyme system is further described by Adler et al. in *J. Bacteriology*, August 1981, p.326–332; and in a manuscript of H. I. Adler dated Aug. 23, 1989 and scheduled to be published in 1990 and entitled "The Use of Microbial Membranes to Achieve Anaerobiosis." All of these references are incorporated by reference herein.

The initial incubation step of the assay invention is carried out for a period of about 5–30 hours at a temperature of from about 25°–35° C. If the target pathogen is present in the sample, and is incubated in an esculin-containing medium, the initial incubation will yield a dark brown or blackened color, because of hydrolysis of the esculin. If no such darkening occurs, the sample is deemed free of the target pathogen.

In the next step of the preferred assay, a small aliquot (e.g., 1 ml.) of the darkened liquid resulting from the initial incubation is placed within one leg of a previously prepared U-shaped KIMAX culture tube. The tube has a central bight section as well as a pair of spaced, upstanding, capped legs. A quantity of semi-solid modified Oxford agar is placed within the central section of the tube. and 1 ml. portions of Fraser Broth supplemented with a small amount of oxyrase enzyme are placed atop the spaced ends of the agar. The modified Oxford agar is a known product and is described in a Beeton Dickinson Microbiology Systems "Product Information Sheet" for the modified agar. A copy of this publication is incorporated by reference herein. This Oxford agar is specially formulated as a selective medium for the isolation of *L. monocytogenes* from specimens containing a mixed flora.

*L. monocytogenes* exhibits a peculiar motility and, in the modified Oxford agar, will gradually move through the agar and eventually darken the Fraser Broth sample in the opposite leg of the culture tube. In particular, after the culture tube is inoculated, incubation is carried out at a temperature from about 30° to 40° C. for a period of about 3-15 hours. If such darkening occurs, it is very, probable that the starting sample is contaminated with *L. monocytogenes*. However, in order to confirm this, the sample is then assayed using conventional confirming assays, such as those described in *Bergey's Manual of Systematic Bacteriology* Vol. 2. Sec. 14. p. 1241.

Although a preferred assay in accordance with the invention involves the screening determination of the presence of *L. monocytogenes* in beef. the invention is not so limited. Thus, this target pathogen may be assayed from samples of other meats such as poultry (e.g. chicken), fish or dairy products. By the same token, other pathogens can also be assayed using the principles of the invention. Such pathogens would include the group consisting of Listeria spp., Salmonella spp., *E. coil, E. coli* 0157:H7, Campylobacter spp. *Campylobacter jejuni*, Yersinia spp., *Campylobacter jejuni*, Yersinia spp., *Yersinia enterocolitica*, and all members of the Family Enterobacteiaceae.

Finally. although the use or an oxygen-reactive enzyme such as oxyrase is, preferred, useful results can be obtained by the use of reducing agents which are effective for creating anaerobic reaction conditions and otherwise enhance the growth of target pathogens in a growth medium. Exemplary reducing agents include L-cysteine, HC1 and titanium (III) citrate.

DESCRIPTION OF THE PREFERRED EMBODIMENTS

EXAMPLE 1

Figure 1:
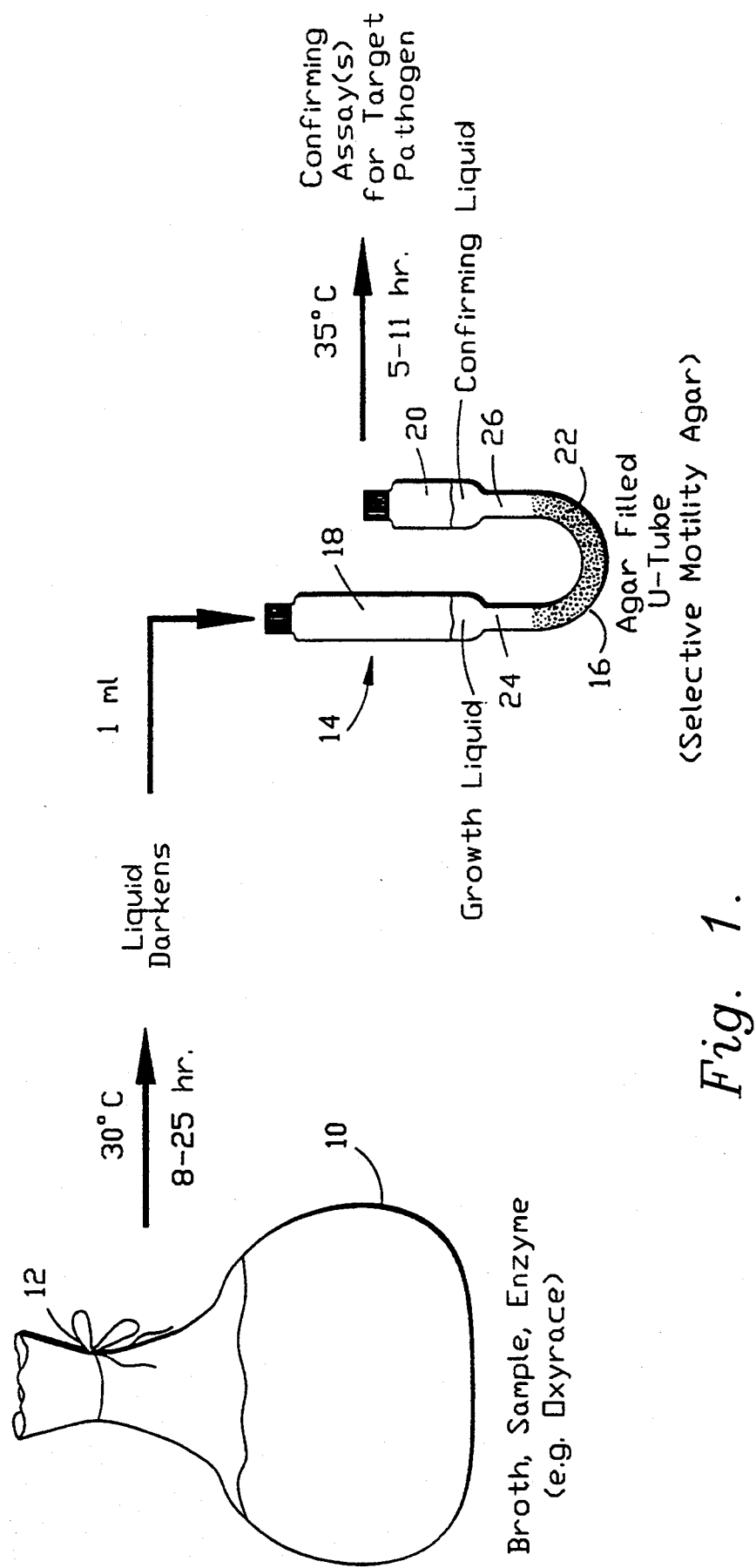
FIG. 1 is a schematic process flow drawing illustrating the preferred assay for the determination of motile facultative anaerobic pathogens.

The most preferred method of detecting *L. monocytogenes* in a sample containing from about 1-100 CFU/g is set forth below, with the FIG. 1 illustration also being referred to as an aid to description. It is to be understood that the following is given for illustrative purposes only and should not be considered as a limitation upon the overall scope of the invention.

First, 25 g. of the beef sample (cut into small pieces) is placed in a conventional anaerobic Stomacher bag 10 (see FIG. 1), along with 0.25 units of oxyrase enzyme and 225 ml. of Fraser Broth. In particular, the Broth is first added to the bag, then the enzyme and finally the meat pieces. The bag 10 is sealed as at 12, and is placed into an incubator at 30° C. The mixture is incubated at that temperature for a period of from about 20-25 hours.

If *L. monocytogenes* is present in the sample, the liquid within the bag will darken to a brownish-black color during the incubation period. This results because of the fact that the target pathogen will metabolize the esculin contained in the broth, yielding the color change.

In the second step, a U-shaped culture tube 14 (such as the KIMAX tube depicted in FIG. 1 having a U-shaped central section 16 and spaced, upstanding capped legs 18, 20) is prepared. In particular, a quantity of the semisolid Oxford modified agar 22 is placed within the section 16, and 1 ml. portions 24. 26 of Fraser Broth supplemented with 0.1 units of oxyrase enzyme are placed atop the agar 22 as growth and confirming liquids respectively. The ends of the tube 14 are then capped to ensure anaerobic conditions.

A 1 ml. sample of the darkened liquid within bag 10 and placed within tube 14, specifically within the liquid portion 24 shown in FIG. 1. The tube is then placed within an incubator at 35° C. for a period of 5-11 hours. *L. monocytogenes* exhibits a type of end-over-end tumbling motility which enables it to travel through the liquid 24 and agar 22. Inasmuch as liquid 24 contains esculin, and the agar contains ferric ammonium citrate and esculin, such characteristic motility may be readily observed by a blackening of liquid 24, progressive blackening of agar 22, and ultimately blackening of liquid 26.

At this point the assay has confirmed the presence of a motile facultative anaerobic pathogen which is quite likely to be *L. monocytogenes*. However, in order to confirm the identity of the pathogen after the foregoing screening assay, a sample of the starting meat product is then subjected to known confirming assays specific for *L. monocytogenes*. Representative confirming assays of this type are described in *Bergey's Manual of Systematic Bacteriology*; Vol. 2, Sec. 14, and particularly p. 1241, which is incorporated by reference herein.

Using the above technique, the following Listeria strains set forth in Table I have been tested, and all such pathogens are detectable in the system.

TABLE I

| | Listeria spp. tested | |
|---|---|---|
| Listeria spp. | Strains | Sources |
| *L. monocytogenes* (14) | 102, 103, 203 | Kansas State University of Veterinary Medicine |
| | LM101M, LM103M, Scott A | University of Wisconsin |
| | Unknown | The Pillsbury Company |
| | Unknown | Russell Research Center |
| | V7, ATCC 35152, LCDC 81-861, Scott A. F 5069 | University of Arkansas |
| | ATCC 1911 ATCC 43259 | ATCC |

TABLE I-continued

| Listeria spp. | Listeria spp. tested Strains | Sources |
|---|---|---|
| L. ivanovii (2) | KC 1714 | University of Arkansas |
|  | ATCC 19919 KC 1714 | Russell Research Center |
| L. innocua (6) | −/−*, +/−*, 5474, 5910-1, 4616, 5618 | The Pillsbury Company |
| L. welshimeri (2) | +/+*, −/+* | Same as above |
| L. seeligeri (1) | Unknown | Same as above |

* = Rhamnose/Xylose sugar fermentations.

The following Table II sets forth assay reaction times observed using the above-described technique on beef samples inoculated with varying concentrations of *L. monocytogenes* strains. In each case the first-stage reaction in the Stomacher bag involved approximately 20 hours incubation time. and thereafter 1 ml. samples of the liquid were placed in the described U-tube filled with agar and liquid. The "Pre-Enrich Time" for each sample was the incubation until a black color was observed in the growth liquid above the agar (i.e. liquid 24 of FIG. 1). The "Thru-Agar Time" was the incubation time observed for the pathogen to pass through the agar. The "Post-Enrich Time", was the time observed until the confirming liquid 26 was blackened in the U-tube. In all instances. the times listed are cumulative.

TABLE II

Detection of *L. monocytogenes* from Inoculated Meats After First Stage Blackening in Fraser Broth

| Strains | Inocula[1] | Pre-Enrich Time (hr.) (1st Side of U-Tube) | Thru-Agar Time (hr.) | Post-Enrich Time (hr.) |
|---|---|---|---|---|
| LM 101M | 210 CFU/ml | 3–4 | 12–13 | 15–16 |
|  | 21 | 5–6 | 14–15 | 17–18 |
|  | 2.1 | 7–8 | 15–16 | 18–19 |
| LM 103M | 340 CFU/ml | 2–3 | 9–10 | 12–13 |
|  | 34 | 4–5 | 10–11 | 13–14 |
|  | 3.4 | 5–6 | 12–13 | 15–16 |
| Scott A | 140 CFU/ml | 3–4 | 14–15 | 17–18 |
|  | 14 | 4–5 | 15–16 | 18–19 |
|  | 1.4 | 4–5 | 14–15 | 18–19 |

[1]Assumed pathogen concentration obtained using standard dilution techniques.

EXAMPLE 2

Figure 2:
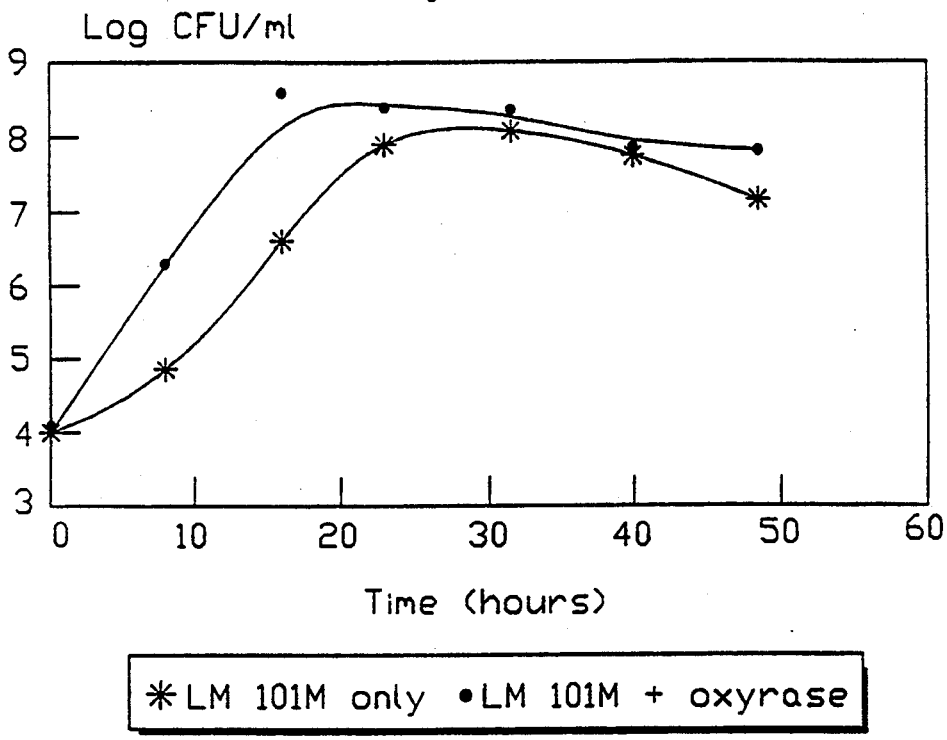
FIG. 2 is a graph illustrating the growth characteristics of the *L. monocytogenes* strain LM 101M in growth medium and in the presence of oxyrase enzyme.
Figure 3:
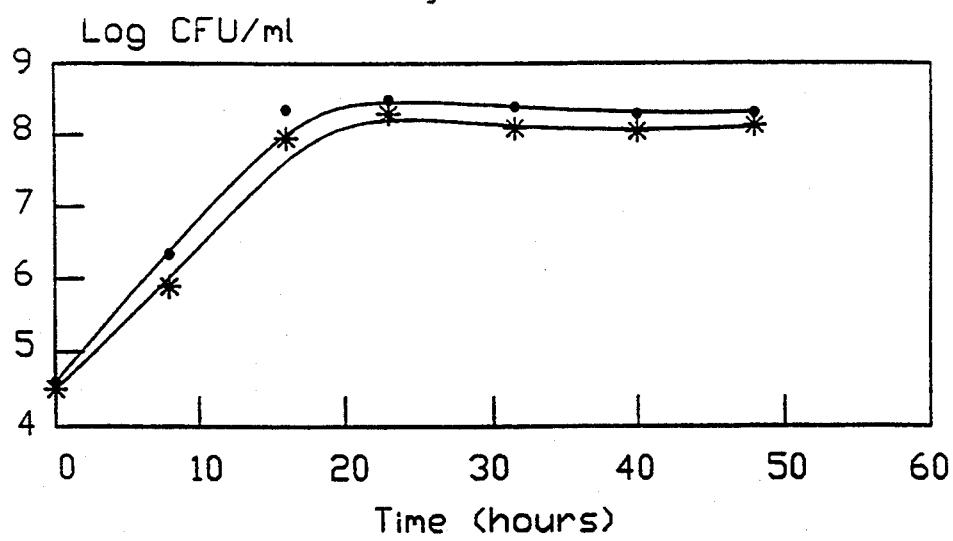
FIG. 3 is a graph illustrating the growth characteristics of the *L. monocytogenes* strain LM 103M in growth medium and in the presence of oxyrase enzyme.
Figure 4:
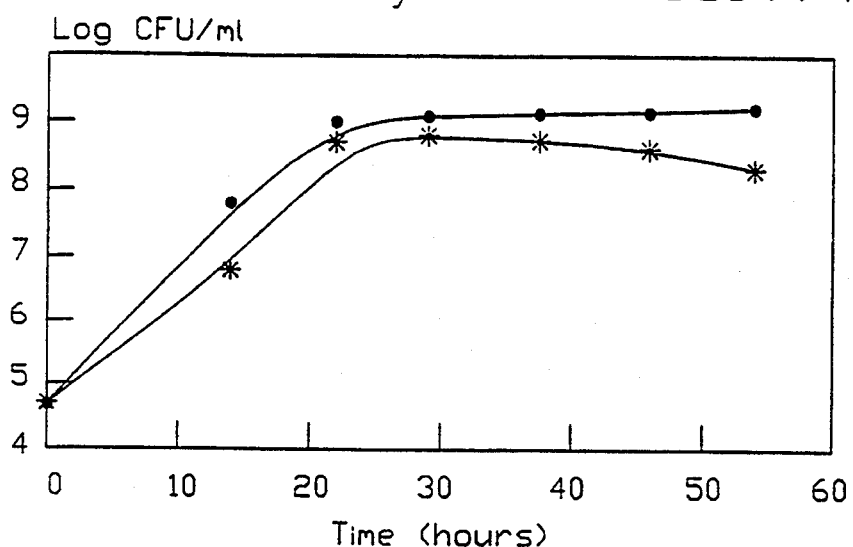
FIG. 4 is a graph illustrating the growth characteristics of the *L. monocytogenes* strain Scott A in growth medium and in the presence of oxyrase enzyme.

A series of tests were undertaken to determine the effect of oxyrase enzyme upon the growth characteristics of various *L. monocytogenes* strains. In all instances the tests were directly comparative, and involved placing identical concentrations of the respective strains in identical quantities of growth medium, followed by incubation at 37° C. for 50 hours. In particular, each strain was tested by placing $10^6$ CFU/ml. of the strain in 100 ml. of Fraser Broth; a comparative test was undertaken using the same concentration of pathogen in the same quantity of Fraser Broth, but with the addition of 10 units of oxyrase enzyme. FIGS. 2–4 graphically depict the results of these comparative tests, and demonstrate significantly faster growth of the *L. monocytogenes* strains in the presence of oxyrase.

EXAMPLE 3

Figure 5:
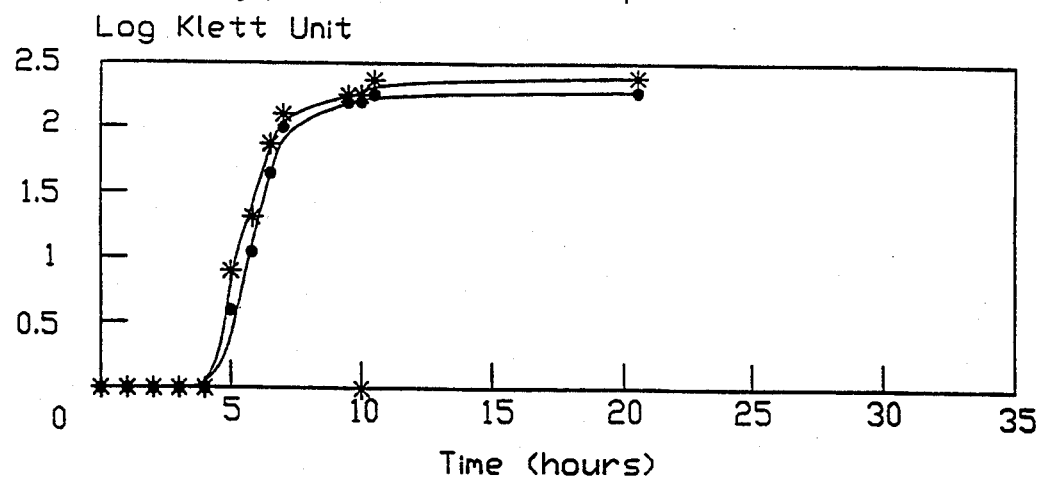
FIG. 5 is a graph similar of that of FIGS. 2-4 but illustrating the effect of oxyrase enzyme on *S. typhimurium* suspended in TSB medium.

In this test, the effects of oxyrase on the growth of *S. typhimurium* suspended in TSB (Tryptic Soy Broth) and incubated at 37° C. for 20 hours. Here again, the test was directly comparative, and involved placement of $10^5$ CFU/ml. of *S. typhimurium* in 100 ml. of TSB, followed by incubation for 20 hours. A comparative sample was identically produced, save for the addition of 10 units of oxyrase enzyme in the TSB. The results of this test are set forth graphically in FIG. 5.

EXAMPLE 4

Figure 6:
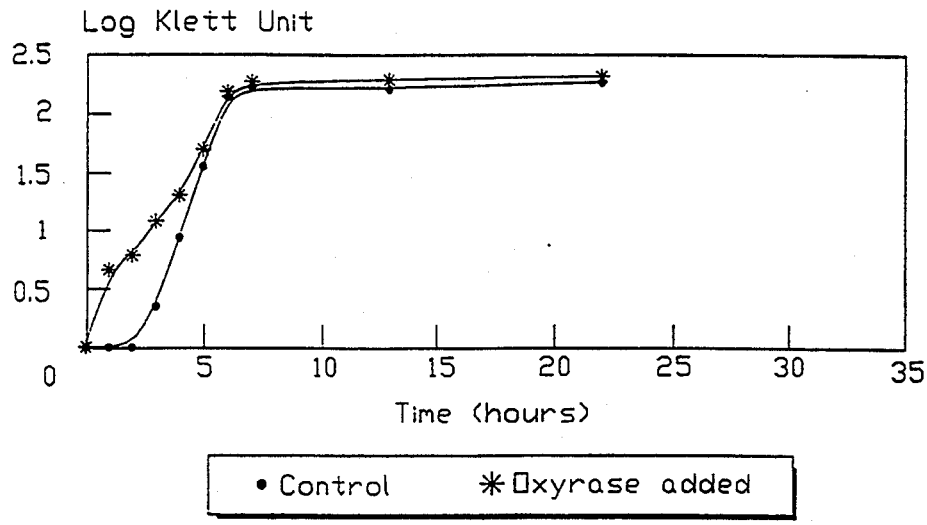
FIG. 6 is a graph illustrating the effect of oxyrase enzyme on a strain of *E. coli* suspended in BHI medium.

This test was another direct comparative study wherein the effect of oxyrase on *E. coli* 0157:H7 suspended in BHI (Brain Heart Infusion Medium). In this case, a controlled sample consisting of $10^5$ CFU/ml. of *E. coli* 0157:H7 was placed in 100 ml. of BHI, followed by incubation at 37° C. for 22 hours. A comparative sample was also compared which was identical except for the addition of 10 units of oxyrase enzyme. This enzyme-added sample was incubated under these same conditions as the control. The results of this test are set forth in FIG. 6.

EXAMPLE 5

In order to determine the effect of oxyrase enzyme on heat injured *L. monocytogene*, the following experiment was undertaken. Specifically, Brain Heart Infusion Broth (BHI, pH 7.4; 200 g calf brain, 50 g beef heart, 10 g protease peptone, 2 g dextrose, 5 g NaCl. and 2.5 g disodium phosphate per liter of distilled water) in a 10 ml. test tube was preheated at 60° C. for 1 hour in a circulating water bath. One ml. of a $10^8$ suspension of *L. monocytogenes* was added to the preheated BHI, shaken, and held in the 60° C. water bath for exactly 15 minutes. The broth was then rapidly cooled in an ice bath.

Figure 7:
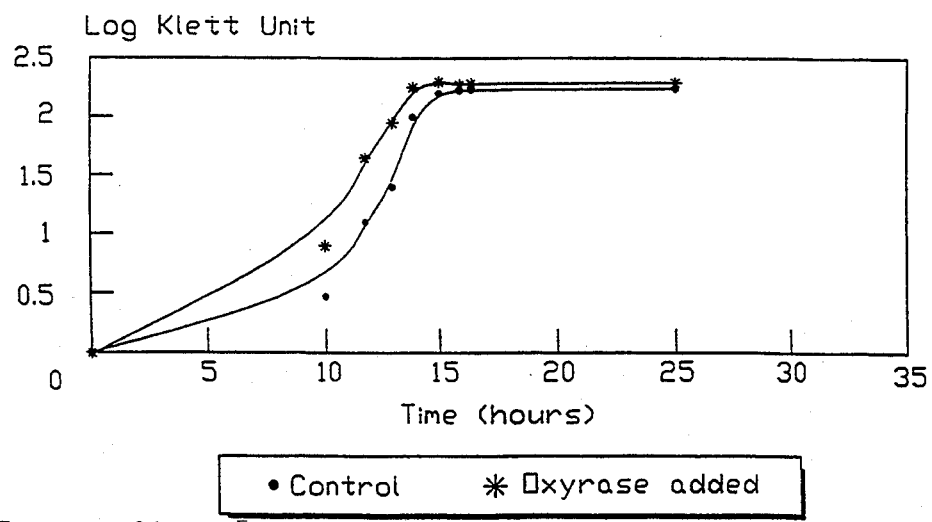
FIG. 7 is a graph illustrating the growth characteristics of heat injured *L. monocytogenes* contacted with oxyrase enzyme in a growth medium.

One ml. of the heat-stressed cells (about $10^4$) was added into 100 ml. of BHI Broth in a Klett flask, and the turbidity of the Broth was measured hourly using a Klett meter, during incubation at 37° C. over a period of 25 hours. A comparative sample was similarly treated, except that it included 10 units of oxyrase enzyme. The results of this test are set forth in FIG. 7, and demonstrate that the presence of oxyrase enhances growth of the injured *L. monocytogenes*.

EXAMPLE 6

In this test the assay of the present invention was directly compared with the prior art FSIS method for the isolation and identification of *L. monocytogenes*. In this experiment, samples of ground beef were inoculated with varying concentrations of the LM 103M strain, and these samples were subjected to the prior art assay and that of the present invention, the latter being described in Example 1.

Table III sets forth the results of these tests, and will be seen that in all instances the U-tube technique of the present invention gave significantly faster assay results, as compared with the prior art method.

TABLE III

| L. monocytogenes | 1000 | 100 | 10 | 1 | 0.1 |
|---|---|---|---|---|---|
| FSIS Prior Art Technique | 7 | 8 | 8 | 9 | 9 |
| Time (hr.) to see black color in Fraser Broth after 24 hr. primary enrichment | 31 to 33 hr. (enrich.) | | + | 24 to 36 hr. (plating) | |
| Total Time | | 55 to 69 hrs. | | | |
| U-Tube Technique | 18 | 20 | 22 | 25 | 26 |
| Time (hr.) to see black color in Fraser Broth + | | + ca. 20 hr. in U-Tubes | | | |
| Total Time | | 38 to 46 hrs. | | | |

EXAMPLE 7

The assay of the invention is highly selective for the determination of motile facultative anaerobic pathogens such as *L. monocytogenes*. A large number of potential competitive pathogens set forth in Table IV below have been determined to exhibit no growth in Fraser Broth. Hence, the presence of these pathogens in a given sample would not detract from the accuracy, of the assay.

TABLE IV

| Pathogens Exhibiting No Growth in Fraser Broth | |
|---|---|
| Acetobacter aceti | Salmonella chameleon |
| Acinetobacter calcoaceticus | Salmonella enteritidis |
| Arizona hinshawii | Salmonella molade |
| Arthrobacter globiformis | Salmonella montevideo |
| Bacillus cereus | Salmonella senftenberg |
| Bacillus subtilis | Salmonella typhimurium |
| Bordatella bronchisetica | Serratia liquefaciens |
| Citrobacter freundii | Serratia rubidaea |
| Hafnia alvei | Shigella boydii |
| Micrococcus luteus | Shigella dysenteriae |
| Propionibacterium sp. | Shigella flexneri |
| Proteus mirabilis | Shigella sonnei |
| Proteus morganii | Staphylococcus albus |
| Proteus strutzer | Staphylococcus aureus |
| Providencia sturartii | |

In addition. the following potentially competitive pathogens (Table V), while exhibiting growth in Fraser Broth, are not motile in the modified Oxford agar, or give a straw color in Fraser Broth. Accordingly, these pathogens likewise do not detract from the specificity of the present assay.

TABLE V

| Growth in Fraser Broth and Appearance of Dark Black Color but No Motility Through U-Tube |
|---|
| Enterobacter aerogenes |
| Enterobacter aerogenes |
| Flavobacterium capsulatum |
| Klebsiella oxytoca |
| Klebsiella pneumoniae |
| Morganella morganii |
| Proteus vulgaricus |
| Pseudomonas aeruginosa |
| Pseudomonas fluorescens |
| Pseudomonas fragi |
| Pseudomana maltophilia |
| Serratia marcescens |
| Streptococcus faecalis |
| Streptococcus lactis |
| Growth in Fraser Broth and Appearance of Straw Color |
| Enterobacter cloacae |

EXAMPLE 8

Figure 8:
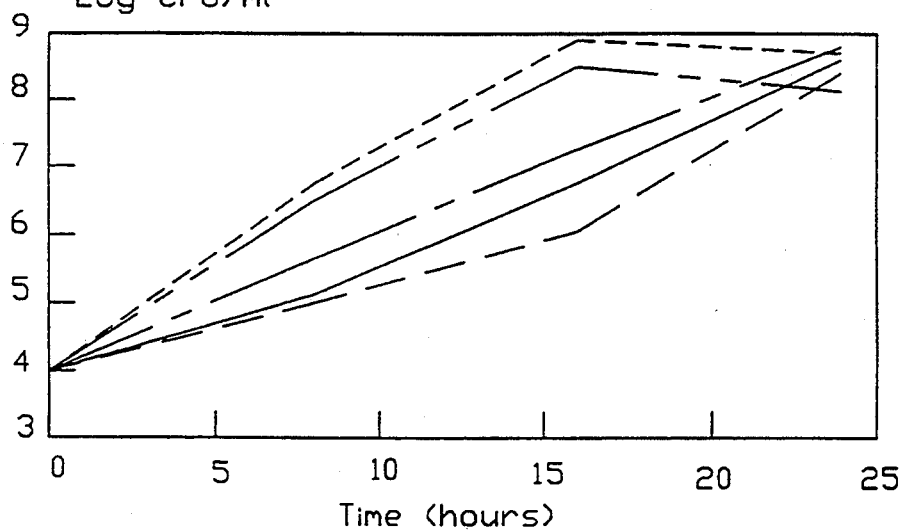
FIG. 8, is a graph illustrating the growth characteristics of *L. monocytogenes* in various growth media supplemented with esculin and iron.

In this Example a number of other selective enrichment broths supplemented with esculin and iron were tested and compared with Fraser Broth, insofar as growth of *L. monocytogenes* therein is concerned. In particular, standard Listeria enrichment broth (LEB), LEB supplemented with 1.0 g/l. esculin and 0.5 g/l. of ferric ammonium citrate, Fraser Broth, University of Vermont Broth (UVM), and UVM supplemented with 0.5 g/l. of ferric ammonium citrate were tested. In each instance 100 ml. of a respective broth was inoculated with $10^4$ CFU/ml. of the LM101M strain of *L. monocytogenes*. The respective samples were then incubated at 37° C. for 24 hours. The results of these series of tests are set forth in FIG. 8, where it will be seen that other growth media provide excellent growth for the pathogen, and could therefore be used in the invention.

EXAMPLE 9

In this test the effectiveness of several reducing agents was measured. In each case $10^3$ CFU/ml. of LM 101M *L. monocytogenes* was inoculated into respective 100 ml. portions of BHI Broth. 0.05% by volume portions of reducing agents were then added to the inoculated broth samples, along with oxyrase enzyme and a control (i.e., no enzyme or reducing agent). The broth samples were then incubated for eight hours at 37° C., and bacterial counts were taken. The results (Table VI) showed that the reducing agents were effective, but the oxyrase enzyme was still superior.

TABLE VI

Effect of Reducing Agents on Growth of *L. monocytogenes* LM 101M in BHI Broth after 8 hour incubation at 37° C.

| Reducing Agent | Number of Cells | Reported $E'_h$ Value |
|---|---|---|
| L-cysteine.HCl | $1.9 \times 10^6$ | −210 mV |
| Titanium III citrate | $1.8 \times 10^6$ | −480 mV |
| Oxyrase | $2.9 \times 10^6$ | −200 to −300 mV |
| Control | $1.4 \times 10^6$ | — |

We claim:

1. In a method of incubating a facultative anaerobic microorganism in order to enhance the growth rate thereof, including the steps of placing the microorganism in a growth medium which supports growth thereof, and causing said microorganism to grow in said growth medium, the improvement which comprises the step of supplementing the growth medium with an effective, growth rate-enhancing amount of free oxyrase enzyme in the growth medium.

2. The method of claim 1, including the step of incubating said microorganism at a temperature of 37° C.

3. The method of claim 1, said growth medium being sterile.

* * * * *